United States Patent [19]

DeLuca et al.

[11] Patent Number: 4,717,721

[45] Date of Patent: Jan. 5, 1988

[54] SIDECHAIN HOMO-VITAMIN D COMPOUNDS WITH PREFERENTIAL ANTI-CANCER ACTIVITY

[75] Inventors: Hector F. DeLuca; Heinrich K. Schnoes, both of Madison, Wis.; Nobuo Ikekawa, Tokyo, Japan; Voula Ostrem, Madison, Wis.

[73] Assignee: Howard W. Bremer, Madison, Wis.

[21] Appl. No.: 739,332

[22] Filed: May 30, 1985

[51] Int. Cl.$^4$ .......................... A61K 31/59; C07J 9/00
[52] U.S. Cl. .................................. 514/167; 260/397.2
[58] Field of Search ...................... 514/167; 260/397.2

[56] References Cited

U.S. PATENT DOCUMENTS 4,391,802  7/1983  Suda et al. ........................ 514/167

FOREIGN PATENT DOCUMENTS 0067423  4/1985  Japan ................................ 514/167

*Primary Examiner*—Leonard Schenkman
*Assistant Examiner*—Joseph A. Lipovsky
*Attorney, Agent, or Firm*—Howard W. Bremer

[57] ABSTRACT

This invention relates to a method for enhancing cell differentiation in malignant cells by exposing the cells to a 1α-hydroxylated vitamin D derivative characterized by a 17-side chain greater in length than the cholesterol or ergosterol side chains.

The method finds application in the treatment of neoplastic diseases including leukemoid diseases and, specifically, leukemia.

10 Claims, No Drawings

SIDECHAIN HOMO-VITAMIN D COMPOUNDS WITH PREFERENTIAL ANTI-CANCER ACTIVITY

This invention was made with Government support under NIH Grant No. AM-14881 awarded by the Department of Health and Human Services. The Government has certain rights in this invention.

DESCRIPTION

1. Technical Field

This invention relates to certain novel vitamin D compounds which are preferentially active in inducing the differentiation of malignant cells to non-malignant cells. More specifically, this invention relates to a method of enhancing the antineoplastic activity of vitamin D compounds by increasing their side-chain length by one carbon, and to a method for using these compounds as anti-cancer agents.

2. Background Art

The importance of hydroxylated forms of vitamin D as regulators of calcium and phosphate metabolism in animals and humans is well-established through many disclosures in the patent and general literature. Vitamin $D_3$, the natural form of the vitamin produced in the skin, is known to be hydroxylated in vivo to 25-hydroxyvitamin $D_3$ (25-OH-$D_3$) and then to 1α,25-dihydroxyvitamin $D_3$ (1α,25-$(OH)_2D_3$), the latter compound being generally regarded as the tissue active hormonal form, responsible for regulating such processes as intestinal calcium absorption, bone mineral resorption, and the maintainance of the appropriate calcium and phosphorus balance in vivo for proper bone formation and the general health of the organism. Another form of vitamin D, namely vitamin $D_2$, which is also commonly used as a food additive or vitamin D supplement, undergoes an analogous hydroxylation sequence and the resulting dihydroxylated form, 1α,25-dihydroxyvitamin $D_2$, likewise expresses potent calcium regulating activity in vivo. Thus, these hydroxylated metabolites as well as certain structural analogs have found, or have been proposed for, many uses in the treatment or prophylaxis of a variety of calcium metabolism disorders and related diseases, such as rickets, renal osteodystrophy, Paget's disease, hyper- and hypoparathyroidism, and osteoporosis, as well as for veterinary applications, such as the milk fever disease, egg shell thinness, or leg weakness in fowl.

More recently it has been discovered that 1α,25-dihydroxyvitamin $D_3$ (1α,25-$(OH)_2D_3$) and its structural analog 1α-hydroxyvitamin $D_3$ (1α-OH-$D_3$), in addition to their well-established calcemic action referred to above, also express potent anti-cancer activity. Specifically, it was shown that the above-named compounds were effective in causing differentiation of malignant human cells, such as leukemia cells in culture, to non-malignant macrophages, and the anti-cancer activity on cells in vitro could be correlated with beneficial effects in vivo by showing that the administration of these compounds extended the life span of leukemic mice (compared to controls) and markedly improved the condition of human leukemia patients. Based on these observations, 1α-hydroxylated vitamin D compounds have been proposed as therapeutic agents for the treatment of leukemoid diseases (Suda et al., U.S. Pat. No. 4,391,802).

Although these known 1α-hydroxyvitamin D compounds tested by Suda et al. (supra), namely 1α-hydroxyvitamin $D_3$ (1α-OH-$D_3$) and 1α,25-dihydroxyvitamin $D_3$ (1α,25-$(OH)_2D_3$), are indeed highly effective in causing differentiation of leukemic cells, a serious disadvantage to their use as antileukemic agents is the inherent, and hence unavoidable high calcemic activity of these substances. Thus, 1α,25-$(OH)_2D_3$, the most potent vitamin-derived antileukemic agent known thus far, is also the most potent calcemic agent, and the antileukemic potency of 1α-OH-$D_3$ is likewise correlated with high calcemic activity. The administration of these compounds, at the dosage level where they are effective as antileukemic drugs (e.g. 1 μg/day as specified in the examples of the Suda et al. patent), would necessarily produce elevated, potentially excessive, calcium levels with attendant serious medical complications, particularly in patients already suffering from debilitating disease. Because of the high intrinsic potency of the known 1α-hydroxyvitamin D compounds in raising calcium levels, their use as antileukemic agents may be precluded.

A preferred method of treatment of malignant disease states clearly would be the administration of compounds characterized by a high antileukemic to calcemic activity ratio, that is, of compounds exhibiting an enhanced potency in causing differentiation of leukemic cells as compared to their potency in raising serum calcium levels.

DISCLOSURE OF INVENTION

A class of 1α-hydroxyvitamin D compounds with the property of an enhanced antileukemic/calcemic activity ratio has now been found. These novel compounds exhibit greater activity in causing differentiation of leukemic cells than compounds known heretofore, but show no enhanced calcemic activity. Specifically, it has been found that by extending the vitamin D side chain by one or more carbons, one obtains side-chain homovitamin D compounds that are more active than 1α,25-dihydroxyvitamin $D_3$ (1α,25-$(OH)_2D_3$) in antineoplastic activity as measured by leukemia cell differentiation, while being no more active, or somewhat less active than 1α,25-dihydroxyvitamin $D_3$ in their effect on calcium metabolism. Because of this unique and unexpected combination of properties, the novel side-chain homovitamin D compounds of this invention represent superior and preferred agents for the treatment of leukemias and other neoplastic diseases.

The compounds having this desirable property are 1α-hydroxy-24-homo- and 1α-hydroxy-26-homovitamin D derivatives characterized by the structures below:

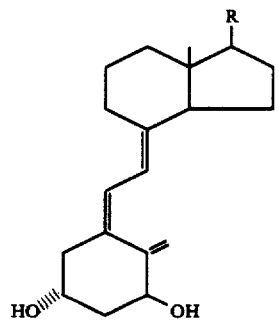

where R is a steroid homo side-chain defined by the structures I, II, III and IV below:

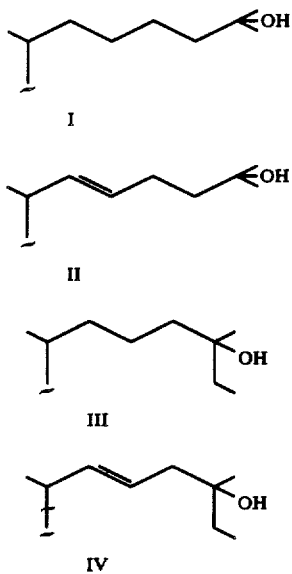

Thus, the compounds identified by structures I and II above are 1α,25-dihydroxy-24-homovitamin D₃ (compound I) and 1α,25-dihydroxy-22E-dehydro-24-homovitamin D₃ (compound II).

The compounds of structures III and IV above are 26-homo-1α-hydroxyvitamin D analogs, which may be named, respectively, 1α,25-dihydroxy-26-homovitamin D₃ (compound III) and 1α,25-dihydroxy-22E-dehydro-26-homovitamin D₃ (compound IV).

When administered to human promyelocytic leukemia cells (HL-60 cells) grown in culture, the side-chain homovitamin D compounds having the structures shown above, induce the differentiation of these cells to macrophages (monocytes). In several standard assays for measuring differentiation activity, these compounds were shown to be more effective than 1α,25-(OH)₂D₃, the most active vitamin D derivative known thus far. These assays were performed as follows:

Assay of homovitamin D compounds for differentiation activity

The human promyelocytic leukemia cell line (HL-60) was maintained in suspension culture in RPM1 1640 medium (Gibco, Grand Island, NY) supplemented with 10% (v/v) heat inactivated fetal calf serum, 100 μg/ml penicillin, 100 μg/ml streptomycin and 0.25 μg/ml fungizone. Cells were cultured in a humidified atmosphere with 5% $CO_2$. Cell viability was assessed by standard assays, e.g. trypan blue exclusion. Morphological evaluations were done on Wright stained slide preparations.

Cells were seeded at $1.5-2 \times 10^5$ cells/ml in 10 ml of medium in tissue culture dishes. After 20 hr, duplicate dishes were then treated with each of the test compounds (i.e. 1α,25-(OH)₂D₃, and compounds I, II, III and IV) at various concentrations as indicated in the tables below. The test compounds were added as solutions in 100% ethanol so that the total ethanol concentration in each culture dish did not exceed 0.2%. Control cultures were treated with the same concentration of ethanol. After four days (96 hr) of incubation with test compounds, the cells were harvested from these culture dishes and cell number and viability were determined. The extent of differentiation induced by the tested vitamin D derivatives was expressed as the percentage of cells that exhibit functional and enzymatic markers characteristic of monocytes. The two markers assayed were (a) the ability of the cells to phagocytize dead yeast, and (b) the ability of the cells to produce superoxide (reduce nitrotetrazalium blue) when stimulated with phorbol esters.

(a) Phagocytosis Assay for Differentiation Activity:

The harvested cells were resuspended in RPM1 medium containing 20% AB serum and 20% fetal calf serum, to give a preparation containing $2 \times 10^6$ cells/ml. To 0.5 ml ($10^6$ cells) of the above cell suspension was then added 0.5 ml of a suspension (in phosphate-buffered saline) of heat-killed saccharomyces cerevisiae cells ($1 \times 10^8$ cells) which had been stained with trypan blue. After incubation of this mixture for 1 hr at 37° C., the number of phagocytic cells was counted (as determined by the trypan blue stained yeast appearing intracellularly) and expressed as a percent of the total viable cells present. This "% phagocytic cells" indicates the percent of differentiation induced by the test compounds. Results are summarized in Table 1 below.

TABLE 1

| | Percent phagocytic (differentiated) cells produced in HL-60 cell cultures treated with vitamin D compounds at various concentrations | | | | | | |
|---|---|---|---|---|---|---|---|
| | Concentration (moles/liter) | | | | | | |
| Compound Administered | $0^{(a,b)}$ | $3 \times 10^{-10}$ | $5 \times 10^{-10}$ | $1 \times 10^{-9(b)}$ | $1 \times 10^{-8(b)}$ | $1 \times 10^{-7(b)}$ | $3 \times 10^{-7}$ |
| 1,25-(OH)₂D₃ | 10 ± 1.5 | 17 | 23 | 28 ± 4 | 47 ± 1 | 67 ± 6 | 69 |
| homo-cpd I | 10 ± 1.5 | 29 | 38 | 47 ± 6 | 69 ± 3 | 77 ± 1 | 78 |
| homo-cpd II | 10 ± 1.5 | 31 | 48 | 51 ± 4 | 69 ± 0.5 | 77 ± 1 | 78 |
| homo-cpd III | 10 ± 1.5 | 28 | 38 | 44 ± 5 | 72 ± 2 | 76 ± 3 | 77 |
| homo-cpd IV | 10 ± 1.5 | 22 | 42 | 48 ± 6 | 70 ± 0 | 78 ± 4 | 83 |

[a]Control level; cell cultures were treated with solvent ethanol only.
[b]Results tabulated in these columns represent the mean ± SEM of three different experiments, each done in duplicate.

The results in Table 1 show that all four homo compounds have very similar differentiation activity, and that all four are significantly more potent than 1,25-(OH)₂D₃. At all concentrations, the homo compounds achieve a greater degree of differentiation of the leukemia cells than 1α,25-(OH)₂D₃, the most active compound known thus far. For example, at a concentration of $10^{-8}$ molar the homo compounds achieve a differentiation of 70%, whereas 1,25-(OH)₂D₃ at the same concentration gives only about 47% differentiated cells. To achieve 50% differentiation requires a concentration of $1 \times 10^{-9}$ M of the homo compounds, but about $1 \times 10^{-8}$ M of 1α,25-(OH)₂D₃, i.e. a difference in potency of about 10-fold.

(b) NBT-Reduction Assay for Differentiation:

This assay depends on the ability of monocyte-like leukemia cells to reduce the nitroblue tetrazolium (NBT) reagent to a black-blue precipitate (formazan)

when stimulated by phorbol esters. The assay was performed according to the general procedure given by Yen et al (J. Cellular Physiol. 118, 277 (1984)). The cells were harvested as above and then suspended in RPMI medium; to 0.2 ml of this suspension (containing about 1.4×10⁶ cells/ml) was added 0.2 ml of the nitroblue tetrazolium (NBT) reagent. (The NBT reagent was prepared by mixing a solution containing 50 mg of nitroblue tetrazolium in 50 ml of phosphate-buffered saline with 10 microliters of an acetone/water (1:1) solution containing 0.5 mg/ml of 4β-phorbol-12-myristate-13-acetate). After standing in a water bath for 30 min, the differentiated cells (i.e. the cells showing formazan blue deposits indicative of NBT reduction) were counted with a hemocytometer and expressed as the percent of total viable cells present. The results of this assay are shown in Table 2 below.

pounds (I or II) dissolved in 0.05 ml of 95% ethanol. Rats in the control group were given 0.05 ml ethanol vehicle in the same manner. Eighteen hours after the dose, the rats were killed and their blood was collected and centrifuged to obtain serum. Serum calcium concentrations were determined in the presence of 0.1% lanthanum chloride with an atomic absorption spectrometer Model 403 (Perkin-Elmer Co., Norwalk, Conn.).

Results obtained are shown in the following Table (Table 3).

TABLE 3

| Compound Administered | Amount Administered (pmol/rat) | Serum Calcium Concentration (mg/100 ml) |
|---|---|---|
| Exp. Ethanol | — | $3.6 \pm 0.3^{(a)*}$ |
| I $1\alpha,25\text{-}(OH)_2D_3$ | 650 | $4.9 \pm 0.2^{(b)}$ |

TABLE 2

Percent of cells in HL-60 cell cultures exhibiting nitroblue tetrazolium (NBT) reduction activity after treatment with Vitamin D Compounds at various concentrations

| Compound Administered | Concentration (moles/liter) | | | | | | |
|---|---|---|---|---|---|---|---|
| | $0^{(a,b)}$ | $3 \times 10^{-10}$ | $5 \times 10^{-10}$ | $1 \times 10^{-9(b)}$ | $1 \times 10^{-8(b)}$ | $1 \times 10^{-7(b)}$ | $3 \times 10^{-7}$ |
| $1,25\text{-}(OH)_2D_3$ | $10 \pm 1.5$ | 15 | 27 | $31 \pm 4$ | $45 \pm 4$ | $69 \pm 7$ | 65 |
| homo-cpd I | $10 \pm 1.5$ | 33 | 39 | $46 \pm 4$ | $72 \pm 1$ | $79 \pm 5$ | 77 |
| homo-cpd II | $10 \pm 1.5$ | 33 | 45 | $52 \pm 5$ | $71 \pm 1$ | $78 \pm 5$ | 79 |
| homo-cpd III | $10 \pm 1.5$ | 27 | 41 | $47 \pm 7$ | $72 \pm 5$ | $79 \pm 2$ | 78 |
| homo-cpd IV | $10 \pm 1.5$ | 22 | 44 | $49 \pm 4$ | $70 \pm 2$ | $79 \pm 5$ | 80 |

[a] Control level; cell cultures treated with solvent ethanol only.
[b] Data represent the mean ± SEM of three separate experiments, each assayed in duplicate.

The results shown in Table 2 again establish that all four homo compounds tested are more active than $1\alpha,25\text{-}(OH)_2D_3$ in inducing the differentiation of human myeloid leukemia cells to normal cells, in vitro and that, as in the previous assay (Table 1) all four homo compounds exhibit very similar potency. To achieve 60% differentiation of the leukemic cells as measured by this NBT reduction assay, requires a concentration of $2 \times 10^{-9}$M of the homo compounds; to achieve the same degree of differentiation with $1\alpha,25\text{-}(OH)_2D_3$ requires a concentration of $3.5 \times 10^{-8}$M—a 17-fold difference in potency.

Thus, both of the above assays confirm the high potency of the homovitamin D compounds in inducing the differentiation of leukemic cells. In addition, the above results show that in this differentiation activity these homovitamin D compounds are 10–20 times more potent than $1\alpha,25\text{-}(OH)_2D_3$.

Calcemic activity of homovitamin D compounds

The effect of the homovitamin D compounds (I, II, III and IV) on calcium metabolism in vivo was assessed by measuring their bone calcium mobilization activity in vitamin D-deficient rats, according to the following protocols.

1. Bone calcium mobilization activities of $1\alpha,25\text{-}(OH)_2\text{-}24\text{-homo-}D_3$ compounds (homovitamin D compounds I and II)

Bone calcium mobilization activity was assayed by measuring the rise in serum calcium levels in vitamin D-deficient animals maintained on a low calcium diet in response to the test compound administered. Male, weanling rats (Holtzman Co., Madison, WI) were fed a low-calcium, vitamin D-deficient diet (Suda et al., J. Nutr. 100, 1049-1050, 1970) and water ad libitum for 3 weeks. The rats were then divided into three groups of 5–6 rats each and were given by intrajugular injection either $1,25\text{-}(OH)_2D_3$ or one of the homovitamin D com-

| | | |
|---|---|---|
| $1\alpha,25\text{-}(OH)_2\text{---}24\text{-homo-}$ vitamin $D_3$ (compound I) | 650 | $4.4 \pm 0.2^{(b)}$ |
| Exp. Ethanol | — | $4.2 \pm 0.1^{(c)}$ |
| II $1\alpha,25\text{-}(OH)_2D_3$ | 325 | $5.0 \pm 0.5^{(d)}$ |
| $1\alpha,25\text{-}(OH)_2\text{---}22E\text{-}$ dehydro-24-homo-$D_3$ (compound II) | 650 | $5.0 \pm 0.5^{(d)}$ |

*Standard deviation of the mean [b] is significantly different from [a], and [d] is significantly different from [c], $p < 0.001$ 2. Bone calcium mobilization activity of $1\alpha,25\text{-}(OH)_2\text{-}26\text{-homo-}D_3$ compounds (homovitamin D compounds III and IV)

Male weanling rats were purchased from Holtzman Co., Madison, WI and fed ad libitum a low calcium, vitamin D-deficient diet as described by Suda et al. (J. Nutr. 100, 1049, 1970) and water for 3 weeks. The rats were then divided into 4 groups of 6 animals each which by intrajugular injection were given, respectively, 650 pmol of either $1\alpha,25\text{-}(OH)_2\text{-}26\text{-homo-}D_3$ (homovitamin D compound III), or $1\alpha,25\text{-}(OH)_2\text{-}(22E)\pm^{22}\text{-}26\text{-homo-}D_3$ (homovitamin D compound IV), or $1\alpha,25\text{-}(OH)_2D_3$ dissolved in 0.05 ml of 95% ethanol, 7 hr prior to sacrifice. The rats in the control group were given 0.05 ml of 95% ethanol in the same manner. They were killed by decapitation, the blood was collected and centrifuged to obtain serum. Serum calcium concentration was determined in presence of 0.1% lanthanum chloride with an atomic absorption spectrophotometer (Perkin-Elmer Model 214). Results are shown in the table below (Table 4).

TABLE 4

| Compound Administered | Serum Calcium Concentration (mg/100 ml) |
|---|---|
| ethanol | $3.4 \pm 0.3^{*(a)}$ |
| $1\alpha,25\text{-}(OH)_2\text{---}26\text{-homo-}D_3$ (compound III) | $4.6 \pm 0.2^{(b)}$ |
| $1\alpha,25\text{-}(OH)_2\text{---}(22E) \pm 22\text{-}26\text{-homo-}D_3$ | $4.6 \pm 0.3^{(b)}$ |

TABLE 4-continued

| Compound Administered | Serum Calcium Concentration (mg/100 ml) |
|---|---|
| (compound IV) 1α,25-(OH)$_2$D$_3$ | 4.5 ± 0.2[b] |

*Standard deviation of the mean; [b] is significantly different from [a], $p < 0.001$ It can be concluded from the foregoing data (Tables 3 and 4) that in the vitamin D-responsive systems of vitamin D-deficient animals, the compounds of this invention exhibited either the same or somewhat lower activity than 1α,25-(OH)$_2$D$_3$.

The above data indicate that extension of the side-chain of 1α,25-dihydroxyvitamin D$_3$ results in products with markedly enhanced potency for inducing the differentiation of leukemic cells to normal macrophages (monocytes) (see Tables 1 and 2), and since this differentiating activity is expressed in the case of human leukemia cells (HL-60), it is clear that these novel homovitamin D compounds can be used effectively against leukemias in human subjects. At the same time, these compounds do not exhibit enhanced calcemic activity, but are rather either as active, or somewhat less active, than 1α,25-(OH)$_2$D$_3$ (Tables 3 and 4). Thus, these homovitamin D compounds are characterized by a high antineoplastic to calcemic activity ratio. By virtue of this novel and desirable biological property, these side-chain homo compounds would function as superior therapeutic agents for the treatment of malignant diseases.

For treatment purposes, these compounds can be formulated as solutions in innocuous solvents, or as emulsions, suspensions or dispersions in suitable and innocuous solvents or carriers, or as pills, tablets or capsules by conventional methods known in the art. Such formulations may also contain other pharmaceutically-acceptable and non-toxic excipients, such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal. For the treatment of human leukemia, the homovitamin D compounds of this invention are administered to subjects in dosages sufficient to induce the differentiation of leukemic cells to macrophages. Suitable dosage amounts are from 0.2 μg to 5 μg per day, it being understood that dosages can be adjusted according to the severity of the disease or the response or the condition of subject as is well-understood in the art.

The preparation of the 1α-hydroxy-24-homovitamin D compounds I and II is illustrated by the reactions of Process Scheme 1, where the product identified by Arabic numeral 14 represents 1α,25-dihydroxy-24-homovitamin D$_3$ (homo compound I) and where product 11 is 1α,25-dihydroxy-22E-dehydro-24-homovitamin D$_3$ (homocompound II). This preparatory process is more specifically described by the following example, where the products identified by Arabic numerals (e.g. 1, 2, 3 . . . etc.) refer to the compounds so numbered in Process Scheme I.

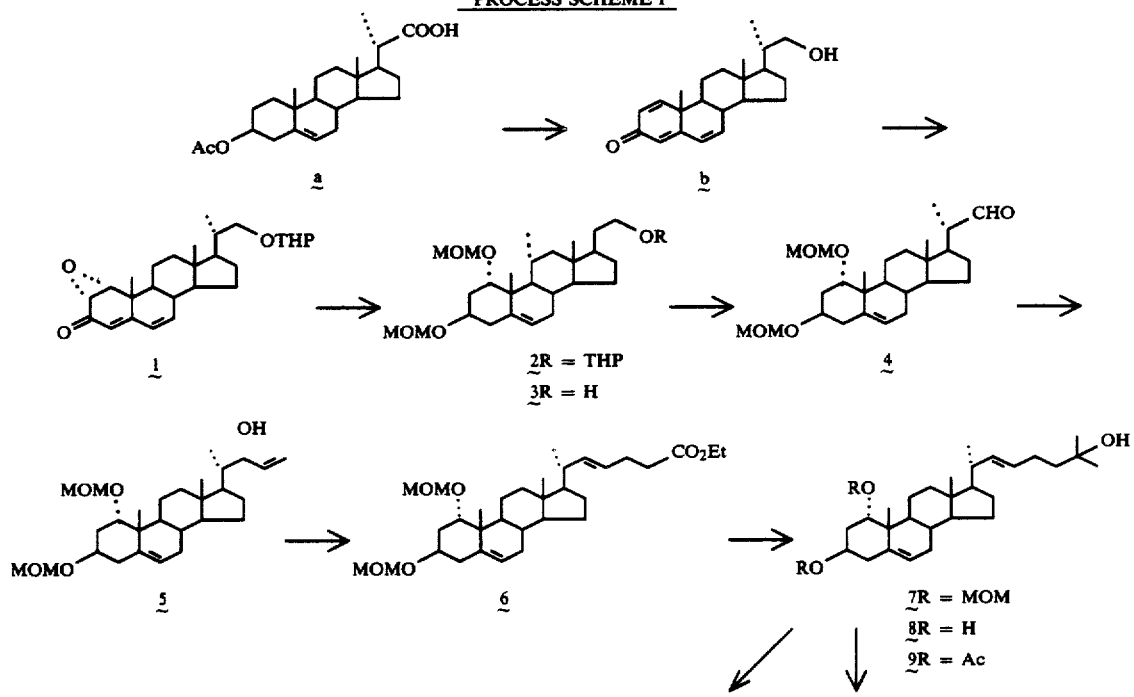

PROCESS SCHEME I

-continued
PROCESS SCHEME I

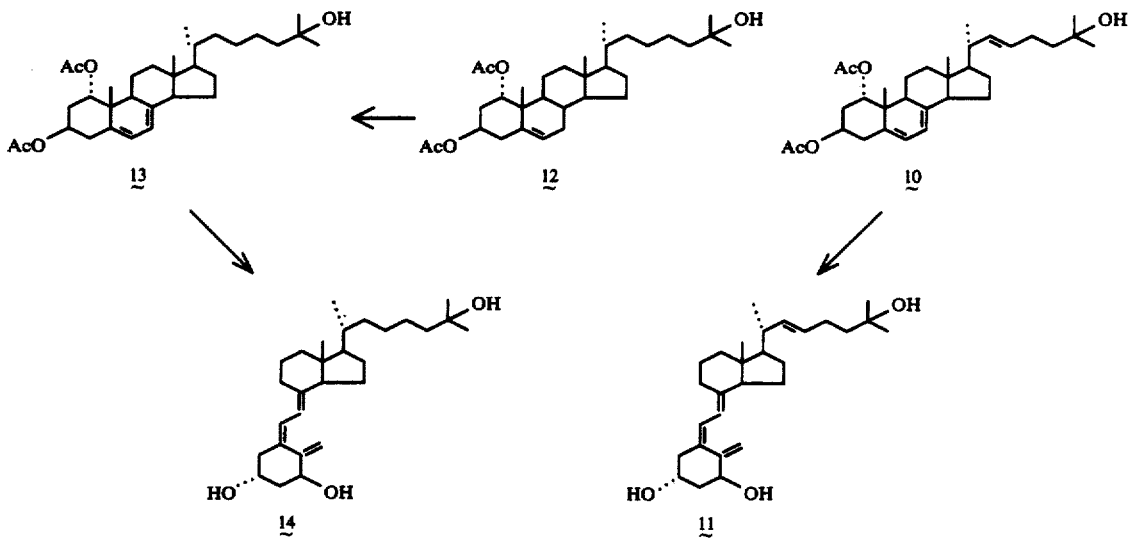

EXAMPLE 1

22-Hydroxy-23,24-dinorchola-1,4,6-triene-3-one (b)

To a solution of 3β-acetoxydinorcholenic acid (a) (7.0 g, 18.04 mmole) in THF (20 mL) lithium aluminum hydride (3.0 g, 78.95 mmole) was added. This mixture was stirred at 60° C. for 14 h. To this reaction mixture water and ethyl acetate were carefully added. Filtration and removal of the solvent gave the residue (5.2 g). This in dioxane (140 mL) was treated with dichlorodicyanobenzoquinone (11.7 g, 51.54 mmole) under reflux for 14 h. After cooling to room temperature the reaction mixture was filtered and the filtrate was evaporated to leave the residue, which was applied to a column of alumina (200 g). Elution with dichloromethane provided the trienone (b) (2.8 g, 47%) mp 156°-157° (ether) UV$\lambda_{max}^{EtOH}$ nm (ε): 299 (13000), 252 (9200), 224 (12000), $^1$H-NMR (CDCl$_3$)δ: 0.80 (3H, s, 18-H$_3$), 1.04 (3H, d, J=6 Hz, 21-H$_3$), 1.21 (3H, s, 19-H$_3$), 3.10-3.80 (3H, m, 22-H$_2$ and OH), 5.90-6.40 (4H, m, 2-H, 4-H, 6-H, and 7-H), 7.05 (1H, d, J=10 Hz, 1-H), MS m/z: 326 (M+), 311, 308, 293, 267, 112.

1α,2α-Epoxy-22-tetrahydropyranyloxy-23,24-dinorchola-4,6-dien-3-one (1)

The alcohol (b) (2.7 g, 8.28 mmole) in dichloromethane (50 mL) was treated with dihydropyrane (1.5 mL, 16.42 mmole) and p-toluenesulfonic acid (50 mg) at room temperature for 1 h. The usual work-up (ethyl acetate for extraction) gave a crude product. To a solution of this product in MeOH (70 mL), 30% H$_2$O$_2$ (4.8 mL) and 10% NaOH/MeOH (0.74 mL) were added and this mixture was stirred at room temperature for 14 h. The usual work-up (ethyl acetate for extraction) gave a crude product, which was applied to a column of silica gel (50 g). Elution with benzene-ethyl acetate (100:1) provided the epoxide (1) (1.45 g, 41%): mp 113°-115° (hexane) UV$\lambda_{max}^{EtOH}$ nm (ε): 290 (22000), $^1$H-NMR (CDCl$_3$)δ: 0.80 (3H, s, 18-H$_3$), 1.07 (3H, d, J=6 Hz, 21-H$_3$), 1.18 (3H, s, 19-H$_3$), 3.38 (1H, dd, J=4 and 1.5 Hz, 1-H), 3.55 (1H, d, J=4 Hz, 2-H), 3.30-4.10 (4H, m, 22-H$_2$ and THP), 4.50 (1H, m, THP), 5.58 (1H, d, J=1.5 Hz, 4-H), 6.02 (2H, s, 6-H and 7-H), MS m/z: 342 (M+-DHP), 324 (M+-THPOH), 309, 283, 85.

1α,3β-Dimethoxymethoxy-23,24-dinorchol-5-en-22-tetrahydropyranyl ether (2)

Lithium (5.00 g) was added in small portion to liquid ammonia (200 ml) at −78° under argon atmosphere during 30 min. After stirring for 1 hr at −78°, 1α,2α-epoxy-22-tetrapyranyloxy-23,24-dinorchola-4,6-diene-3-one (1) (2.00 g, 4.69 m mol) in dry THF (150 ml) was added dropwise at −78° during 30 min, and this mixture was stirred for 1 hr at −78°. To this reaction mixture, anhydrous NH$_4$Cl (60 g) was added in small portion at −78° during 1 hr. After 1.5 hr the cooling bath was removed and most of the ammonia was removed by bubbling argon. The usual work-up (ether was used as a solvent) gave a crude product. This was treated with chloro-methyl methyl ether (2.0 ml, 26.34 m mol) and N,N-diethylcyclohexylamine (4.6 ml, 24.93 m mol) in dioxane (20 ml) at 45° for 24 hr. The usual work-up (ethyl acetate) gave a crude product, which was applied to a column of silica gel (40 g). Elution with hexane-ethyl acetate (5:1) provided the dimethoxymethyl ether (2) (922 mg, 38%) as an oil. $^1$H-NMR δ0.70 (3H, s, 18-H$_3$), 1.02 (3H, s, 19-H$_3$), 1.04 (3H, d, J=6 Hz, 21-H$_3$), 3.34 (3H, s, —O—CH$_3$), 3.37 (3H, s, —O—CH$_3$), 4.63 (2H, ABq, J=7 Hz, ΔAB=11 Hz, 1α—O—CH$_2$—O—), 4.64 (2H, s, 3β—O—CH$_2$—O—), and 5.50 (1H, m, 6-H).

1α,3β-Dimethoxymethoxy-23,24-dinorchol-5-en-22-ol (3)

The THP ether (2) (922 mg, 1.77 mmol) in THF (8 ml) and MeOH (8 ml) was treated with 2M HCl (1 ml) at room temperature for 2 h. The usual work-up (ethyl acetate) gave a crude product, which was applied to a column of silica gel (40 g). Elution with hexane-ethyl acetate (2:1) gave the alcohol (3) (678 mg, 88%) as an amorphous solid. $^1$H-NMR δ0.70 (3H, s, 18-H$_3$), 1.02 (3H, s, 19-H$_3$), 1.04 (3H, d, J=6 Hz, 21-H$_3$), 3.34 (3H, s, —O—CH$_3$), 3.38 (3H, s, —O—CH$_3$), 4.65 (2H, ABq, J=7 Hz, ΔAB=11 Hz, 1α—O—CH$_2$—O—), 4.66 (2H, s, 3β—O—CH$_2$—O—), 5.53 (1H, m, 6-H).

1α,3β-Dimethoxymethoxy-23,24-dinorchol-5-en-22-al (4)

To a solution of oxalyl chloride (0.27 ml, 3.09 mmol) in dichloromethane (8 ml) dimethyl sulphoxide (0.44 ml, 6.21 mmol) was added at −78° C. under argon. The mixture was stirred at −78° C. for 10 min. To the solution the alcohol (3) (660 mg, 1.51 mmol) in dichloromethane (5 ml) was added at −78° C. After stirring for 15 min, triethylamine (1.89 ml, 13.6 mmol) was added. The mixture was stirred at −78° C. under argon for 5 min, and warmed up to room temperature. The usual work-up (ether) gave a crude product, which was applied to a column of silica gel (30 g). Elution with hexane-ethyl acetate (4:1) gave the aldehyde (4) (607 mg, 92%) as a crystal. mp 71°–72° C. (hexane), $^1$H-NMR δ0.74 (3H, s, 18-H$_3$), 1.04 (3H, s, 19-H$_3$), 1.12 (3H, d, J=6 Hz, 21-H$_3$), 3.35 (3H, s, —O—CH$_3$), 3.39 (3H, s, —O—CH$_3$), 3.7 (1H, m, 1β-H), 4.65 (2H, ABq, J=7 Hz, ΔAB=11 Hz, 1α—O—CH$_2$—O—), 4.66 (2H, s, 3β—O—CH—O—), 5.52 (1H, m, 6-H), and 9.61 (1H, d, J=3 Hz, —CHO), Anal. Calcd for C$_{26}$H$_{42}$O$_5$: C, 71:85; H, 9.74. Found: C, 71.71; H, 9.68.

1α,3β-Dimethoxymethoxychola-5,23-dien-22-ol (5)

To magnesium (70 mg, 2.92 mmol) in THF (3 ml) 50% solution of vinyl bromide in THF (0.42 ml, 2.98 mmol) was added. The mixture was stirred at room temperature under argon for 30 min. To the resulting Grignard reagent the aldehyde (4) (595 mg, 1.37 mmol) in THF (6 ml) was added at room temperature. The mixture was stirred at room temperature for 1 h. The usual work-up (ether) gave a crude product, which was applied to a column of silica gel (30 g). Elution with hexane-ethyl acetate (3:1) gave the allylic alcohol (5) (595 mg, 94%) as an amorphous solid. $^1$H-NMR δ: 0.70 (3H, s, 18-H$_3$), 1.02 (3H, s, 19-H$_3$), 3.35 (3H, s, —O—CH$_3$), 3.38 (3H, s, —O—CH$_3$), 3.69 (1H, m, 1β-H), 4.20 (1H, m, 22-H), 4.64 (2H, ABq, J=7 Hz, ΔAB=11 Hz, 1α—O—CH$_2$—O—), 4.65 (2H, s, 3β—O—CH$_2$—O—), 5.52 (1H, m, 6-H), 4.90–6.0 (3H, m, 23-H and 24-H$_2$).

(22E)-1α,3β-Dimethoxymethoxy-27-norcholesta-5,22-dien-26-oic acid ethyl ester (6)

A solution of the allylic alcohol (5) (590 mg, 1.28 mmol), triethyl orthoacetate (1.0 ml, 5.46 mmol), propionic acid (4 drops), and xylene (8 ml) was refluxed under argon for 2 h. Removal of the solvent under reduced pressure gave the residue, which was applied to a column of silica gel (30 g). Elution with hexane-ethyl acetate (4:1) gave the ester (6) (630 mg, 93%) as an oil. $^1$H-NMR δ: 0.68 (3H, s, 18-H$_3$), 0.97 (3H, d, J=6 Hz, 21-H$_3$), 1.03 (3H, s, 19-H$_3$), 1.24 (3H, t, J=7 Hz, —CO$_2$CH$_2$CH$_3$), 3.35 (3H, s, —O—CH$_3$), 3.39 (3H, s, —O—CH$_3$), 3.70 (1H, m, 1β-H), 4.11 (2H, q, J=7 Hz, —CO$_2$CH$_2$CH$_3$), 4.64 (2H, ABq, J=7 Hz, ΔAB=11 Hz, 1α—O—CH$_2$—O—), 4.65 (2H, s, 3β—O—CH$_2$—O—), 5.29 (2H, m, 22-H and 23-H), 5.52 (1H, m, 6-H).

(22E)-1α,3β-Dimethoxymethoxy-24-homo-cholesta-5,22-diene-25-ol (7)

To a solution of the ester (6) (605 mg, 1.14 mmol) in THF (6 ml) 1M solution of methylmagnesium bromide in THF (4.5 ml, 4.5 mmol) was added at room temperature. The mixture was stirred at room temperature for 1 h. The usual work-up (ether) gave a crude product, which was applied to a column of silica gel (30 g). Elution with hexane-ethyl acetate (3:1) gave the alcohol (7) (548 mg, 93%) as an oil. $^1$H-NMR δ: 0.68 (3H, s, 18-H$_3$), 0.97 (3H, d, J=6 Hz, 21-H$_3$), 1.01 (3H, s, 19-H$_3$), 1.21 (6H, s, 26-H$_3$ and 27-H$_3$), 3.33 (3H, s, —O—CH$_3$), 3.38 (3H, s, —O—CH$_3$), 3.70 (1H, m, 1β-H), 4.64 (2H, ABq, J=7 Hz, ΔAB=11 Hz, 1α—O—CH$_2$—O—), 4.65 (2H, s, 3β—O—CH$_2$—O—), 5.29 (2H, m, 22-H and 23-H), and 5.50 (1H, m, 6-H).

(22E)-24-Homocholesta-5,22-diene-1α,3β,25-triol (8)

A solution of the dimethoxymethyl ether (7) (540 mg, 1.04 mmol) in THF (15 ml) was treated with 6M HCl (3 ml) at 50° C. for 2.5 h. The usual work-up (ethyl acetate) gave a crude product, which was applied to a column of silica gel (20 g). Elution with hexane-ethyl acetate (1:1) gave the triol (8) (428 mg, 95%) as a crystal. mp 164°–166° C. (hexane-ethyl acetate), $^1$H-NMR δ: 0.68 (3H, s, 18-H$_3$), 0.95 (3H, s, J=6 Hz, 21-H$_3$), 1.00 (3H, s, 19-H$_3$), 1.20 (6H, s, 26-H$_3$ and 27-H$_3$), 3.80 (1H, m, 1β-H), 3.92 (1H, m, 3α-H), 5.30 (2H, m, 22-H and 23-H), and 5.53 (1H, m, 6-H).

(22E)-1α,3β-Diacetoxy-25-hydroxy-24-homocholesta-5,22-diene (9)

A solution of the triol (8) (395 mg, 0.919 mmol) in pyridine (2 ml) was treated with acetic anhydride (1 ml) at room temperature for 16 h. The usual work-up (ethyl acetate) gave a crude product, which was applied to a column of silica gel (20 g). Elution with hexane-ethyl acetate (2:1) gave the diacetate (9) (361 mg, 77%) as an oil. $^1$H-NMR δ: 0.67 (3H, s, 18-H$_3$), 0.97 (3H, d, J=6 Hz, 21-H$_3$), 1.07 (3H, s, 19-H$_3$), 1.21 (6H, s, 26-H$_3$ and 27-H$_3$), 2.01 (3H, s, acetyl), 2.04 (3H, s, acetyl), 4.98 (1H, m, 3α-H), 5.05 (1H, m, 1β-H), 5.31 (2H, m, 22-H and 23-H), and 5.52 (1H, m, 6-H).

(22E)-1α,3β-Diacetoxy-25-hydroxy-24-homocholesta-5,7,22-triene (10)

A solution of the 5-ene (9) (51 mg, 0.0992 mmol) and N-bromo-succinimide (21 mg, 0.118 mmol) in carbontetrachloride (3 ml) was refluxed under argon for 20 min. After the mixture had been cooled to 0° C., the resulting precipitate was filtered off. The filtrate was concentrated below 40° C. to leave the residue. This in THF (5 ml) was treated with a catalytic amount of tetra-n-butylammonium bromide at room temperature for 50 min. Then, the mixture was treated with a solution of tetra-n-butylammonium fluoride in THF (3.5 ml, 3.5 mmol) at room temperature for 30 min. The usual work-up (ethyl acetate) gave a crude product, which was submitted to preparative thin layer chromatography (hexane-ethyl acetate, 4:1, developed five times). The band of Rf value 0.48 was scraped off and eluted with ethyl acetate. Removal of the solvent provided the 5,7-diene (10) 12.5 mg, 24%), UVλ$_{max}^{EtOH}$: 293, 282, and 271.

1α,25-Dihydroxy-22E-dehydro-24-homovitamin D$_3$ (11)

A solution of the 5,7-diene (10) (7.3 mg, 0.0143 mmol) in benzene (90 ml) and ethanol (40 ml) was irradiated with with a medium pressure mercury lamp through a Vycol filter at 0° C. under argon for 5 min. The reaction mixture was refluxed under argon for 1 h. Removal of the solvent under reduced pressure gave a crude product, which was submitted to preparative thin layer chromatography (hexane-ethyl acetate, 4:1, developed five times). The band of Rf value 0.38 was scraped off and eluted with ethyl acetate. Removal of the solvent gave the vitamin $D_3$ diacetate (1.8 mg, 25%). The band of Rf value 0.43 was scraped off and eluted with ethyl acetate. Removal of the solvent recovered the 5,7-diene (10) (2.1 mg, 29%).

The vitamin $D_3$ diacetate (1.8 mg, 2.15 μmol) in THF (4 ml) was treated with 5% KOH/MeOH (1 ml) at room temperature for 20 min. The usual work-up (ethyl acetate) gave a crude product, which was submitted to preparative thin layer chromatography (hexane-ethyl acetate, 1:2, developed three times). The band of Rf value 0.43 was scraped off and eluted with ethyl acetate. Removal of the solvent gave the vitamin $D_3$ analogue (11) (1.4 mg, 90%). The purity of the product (11) was determined as 100% by high performance liquid chromatography (a Shimadzu LC-3A; column, Zorbax ZIL normal phase, 4.6 mm i.d. ×15 cm; solvent, MeOH—$CH_2Cl_2$, 1:49; flow rate, 3 ml/min; retention time, 11.5 min). The vitamin $D_3$ analogue (11) had the following spectral data; $UV\lambda_{max}{}^{EtOH}$: 265 nm, $\lambda_{min}{}^{EtOH}$: 228 nm, MS m/z: 428 (M+), 410, 392 (base peak), 374, 287, 269, 251, 152, 134, 123, 59, $^1$H-NMR (360 MHz) δ: 0.55 (3H, s, 18-$H_3$), 1.02 (3H, d, J=6.6 Hz, 21-$H_3$), 1.22 (6H, s, 26-$H_3$ and 27-$H_3$), 2.32 (1H, dd, J=13.2 and 6.7 Hz), 2.60 (1H, dd, J=13.0 and 3.0 Hz), 2.83 (1H, dd, J=12.0 and 3.0 Hz), 4.23 (1H, m, $W_{\frac{1}{2}}$=18.4 Hz, 3α-H), 4.43 (1H, m, $W_{\frac{1}{2}}$=16.9 Hz, 1β-H), 5.00 (1H, bs, $W_{\frac{1}{2}}$=3.2 Hz, 19-H), 5.30 (1H, dd, J=15.0 and 7.1 Hz, 22-H or 23-H), 5.33 (1H, bs, $W_{\frac{1}{2}}$=3.2 Hz, 19-H), 5.37 (1H, dd, J=15.0 and 5.8 Hz, 22-H or 23-H), 6.01 (1H, d, J=11.0 Hz, 7-H), 6.32 (1H, d, J=11.0 Hz, 6-H).

1α,3β-Diacetoxy-24-homocholest-5-en-25-ol (12)

A mixture of the 5,22-diene (9) (40 mg, 0.0778 mmol) and 10% Pd-C (4 mg) in ethyl acetate (2 ml) was stirred at room temperature under hydrogen for 3 h. The Pd catalyst was filtered off and the filtrate was concentrated to leave the residue, which was applied to a column of silica gel (5 g). Elution with hexane-ethyl acetate (4:1) gave the 5-ene (12) (37 mg, 92%) as an oil. $^1$H-NMR δ: 0.66 (3H, s, 18-$H_3$), 1.08 (3H, s, 19-$H_3$), 1.20 (6H, s, 26-$H_3$ and 27-$H_3$), 2.02 (3H, s, acetyl), 2.05 (3H, s, acetyl), 4.97 (1H, m, 3α-H), 5.07 (1H, m, 1β-H), 5.53 (1H, m, 6-H).

1α,3β-Diacetoxy-24-homocholesta-5,7-dien-25-ol (13)

The 5-ene (12) (19 mg, 0.037 mmol) was converted, as described for (10), to the 5,7-diene (13) (5.8 mg, 31%). $UV\lambda_{max}{}^{EtOH}$: 293, 282, 271 nm.

1α,25-Dihydroxy-24-homovitamin $D_3$ (14)

The 5,7-diene (13) (5.8 mg, 0.0113 mmol) was converted, as described for (11), to the vitamin $D_3$ analogue (14) (890 μg, 19%). The retention time of (14) under the above-described HPLC condition was 11.0 min. $UV\lambda_{max}{}^{EtOH}$: 265 nm, $\lambda_{min}{}^{EtOH}$: 228 nm. MS m/z 430 (M+), 412, 394 (base peak, 376, 287, 269, 251, 152, 134, 59.

If desired, the compounds of this invention can be readily obtained in crystalline form by crystallization from suitable solvents, e.g. hexane, ethers, alcohols, or mixtures thereof as will be apparent to those skilled in the art.

The preparation of the 1α-hydroxy-26-homovitamin D compounds III and IV is given by the reactions of Process Scheme 2, in which product 11 represents 1α,25-dihydroxy-26-homovitamin $D_3$ (homo compound III) and product 8 represents 1α,25-dihydroxy-22E-dehydro-26-homovitamin $D_3$ (homo compound IV). This process is more specifically described by the following example. In this example the products identified by Arabic numbers (e.g. 1, 2, 3 ... etc.) refer to the compounds so numbered in Process Scheme II.

PROCESS SCHEME II

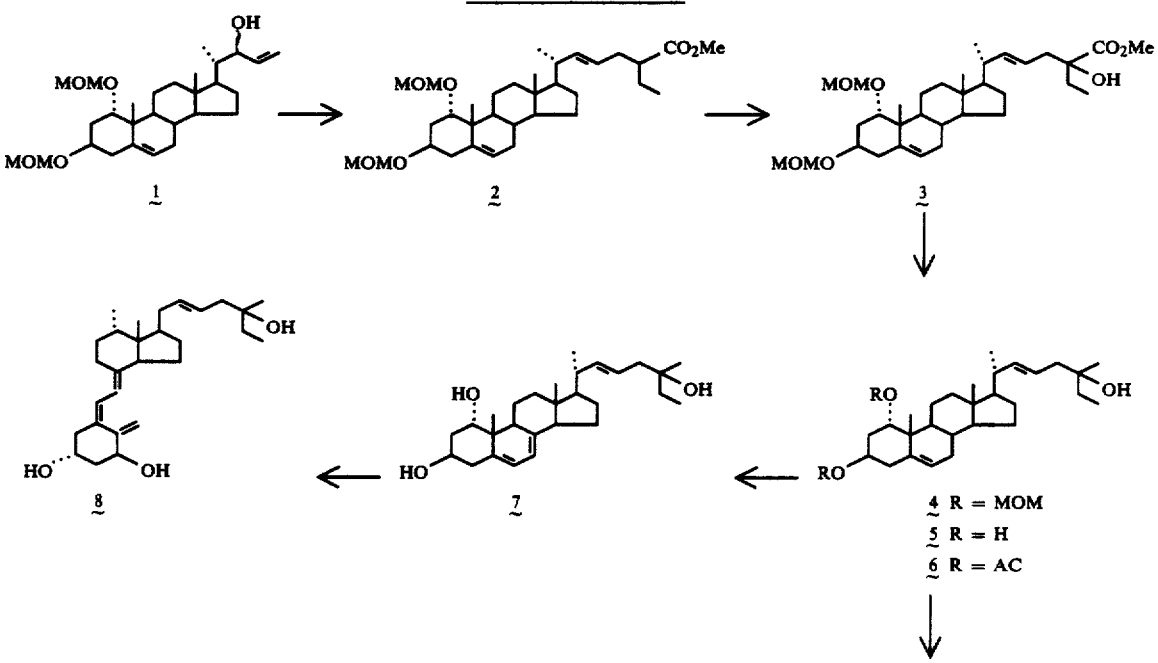

-continued
PROCESS SCHEME II

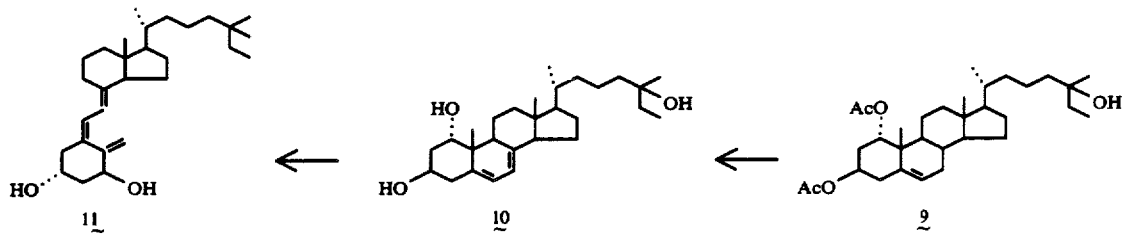

EXAMPLE 2

(22E,25ξ)-1α,3β-Dimethoxymethyloxy-26-homocholesta-5,22-dien-27-oic acid methyl ester (2)

A solution of the allylic alcohol (1) (390 mg, 0.844 mmol), trimethyl ortho-n-butylate (0.7 ml) and propionic acid (3 drops) in toluene (6 ml) was refluxed under argon for 2 hr. Removal of the solvent under reduced pressure gave a crude product, which was applied to a column of silica gel (20 g). Elution with hexane-ethyl acetate (5:1) gave the ester (2) (446 mg, 97%) as an oil. $^1$H-NMR δ: 0.68 (3H, s, 18-H$_3$), 0.88 (3H, t, J=7 Hz, —CH$_2$CH$_3$), 0.98 (3H, d, J=6 Hz, 21-H$_3$) β.03 (3H, s, 19-H$_3$), 3.38 (3H, s, —OCH$_3$), 3.43 (3H, s, —OCH$_3$), 3.68 (3H, s, —CO$_2$CH$_3$), 3.76 (1H, m, 1β-H), 4.68 (2H, s, 3β—O—CH$_2$—O—), 4.69 (2H, ABq, J=7 Hz, ΔAB=11 Hz, 1α—O—CH$_2$—O), 5.27 (2H, m, 22-H and 23-H), and 5.56 (1H, m, 6-H).

(22E,25ξ)-1α,3β-Dimethoxymethyloxy-25-hydroxy-26-homocholesta-5,22-dien-27-oic acid methyl ester (3)

To a solution of LDA (prepared with diisopropylamine (0.13 ml, 0.929 mmol), 1.56M n-butyllithium (0.59 ml) and THF (2 ml), the ester (2) (437 mg, 0.800 mmol) in THF (5 ml) was added and the mixture was stirred under argon at −78° C. for 30 min. Oxygen was bubbled into this solution and then triethylphosphite (0.14 ml, 0.817 mmol) was added. The usual work-up (ether for extraction) gave a crude product, which was applied to a column of silica gel (25 g). Elution with hexane-ethyl acetate (5:1) provided the hydroxy ester (3) (303 mg, 67%) as an oil. $^1$H-NMR δ: 0.68 (3H, s, 18-H$_3$), 0.85 (3H, t, J=7 Hz, —CH$_2$CH$_3$), 0.98 (3H, d, J=6 Hz, 21-H$_3$), 1.02 (3H, s, 19-H$_3$), 3.08 (1H, bs, W$_1$=3 Hz, —OH), 3.38 (3H, s, —OCH$_3$), 3.42 (3H, s, —OCH$_3$), 3.76 (3H, s, —CO$_2$CH$_3$), 4.68 (2H, s, 3β—O—CH$_2$—O—), 4.68 (2H, ABq, J=7 Hz, ΔAB=11 Hz, 1α—O—CH$_2$—O—), 5.32 (2H, m, 22-H and 23-H), 5.55 (1H, m, 6-H).

(22E,25ξ)-1α,3β-Dimethoxymethyloxy-25-hydroxy-26-homocholesta-5,22-diene (4)

To a solution of the hydroxyester (3) (294 mg, 0.539 mmol) in THF (5 ml), lithium aluminum hydride (20 mg, 0.526 mmol) was added and this mixture was stirred at room temperature for 30 min. The usual work-up (ether for extraction) gave a crude diol. This was treated with methane-sulfonyl chloride (0.04 ml, 0.517 mmol) and pyridine (1.5 ml) at room temperature for 30 min. The usual work-up (ether for extraction) gave a crude mesylate. To a solution of the crude mesylate in THF (5 ml), lithium aluminum hydride (20 mg, 0.526 mmol) was added and the mixture was refluxed for 30 min. The usual work-up (ether for extraction) gave a crude product, which was applied to a column of silica gel (20 g). Elution with hexane-ethyl acetate (5:1) provided the alcohol (4) (190 mg, 70%) as an oil. $^1$H-NMR δ: 0.71 (3H, s, 18-H$_3$), 0.90 (3H, t, J=7 Hz, —CH$_2$CH$_3$), 1.03 (3H, d, J=6 Hz, 21-H$_3$), 1.03 (3H, s, 19-H$_3$), 1.12 (3H, s, 27-H$_3$), 3.36 (3H, s, —OCH$_3$) 3.40 (3H, s, —OCH$_3$), 3.74 (1H, m, 1β-H), 4.66 (2H, s, 3β—O—CH$_2$—O—), 4.67 (2H, ABq, J=7 Hz, ΔAB=11 Hz, 1α—O—CH$_2$—O—), 5.35 (2H, m, 22-H and 23-H) and 5.54 (1H, m, 6-H).

(22E,25ξ)-1α,3β,25-Trihydroxy-26-homocholesta-5,22-diene (5)

A solution of the dimethoxymethyl ester (4) 181 mg, 0.349 mmol) in THF (5 ml) was treated with 6N HCl (1 ml) at 50° C. for 1.5 hr. The usual work-up (ethyl acetate for extraction) gave a crude product, which was applied to a column of silica gel (15 g). Elution with hexane-ethyl acetate (1:2) provided the triol (5) (147 mg, 98%), m.p. 85°–87° C. (hexane-dichloromethane). $^1$H-NMR δ: 0.69 (3H, s, 18-H$_3$), 0.89 (3H, t, J=7 Hz, —CH$_2$CH$_3$), 1.02 (3H, s, 19-H$_3$), 1.13 (3H, s, 27-H$_3$), 3.85 (1H, m, 1β-H), 3.98 (1H, m, 3α-H), 5.40 (2H, m, 22-H and 23-H), and 5.60 (1H, m, 6-H).

(22E,25ξ)-1α,3β-Diacetoxy-25-hydroxy-26-homocholesta-5,22-diene (6)

A solution of the triol (5) (100 mg, 0.233 mmol) in pyridine (1 ml) was treated with acetic anhydride (1 ml) at room temperature for 15 hr. The usual work-up (ethyl acetate for extraction) gave a crude product, which was applied to a column of silica gel (10 g). Elution with hexane-ethyl acetate (5:1) provided the diacetate (6) (101 mg, 85%) as an amorphous solid. $^1$H-NMR δ: 0.68 (3H, s, 18-H$_3$), 0.88 (3H, t, J=7 Hz, —CH$_2$CH$_3$), 0.98 (3H, d, J=6 Hz, 21-H$_3$), 1.08 (3H, s, 19-H$_3$), 1.12 (3H, s, 27-H$_3$), 2.03 (3H, s, acetyl), 2.06 (3H, s, acetyl), 4.98 (1H, m, 3α-H), 5.06 (1H, m, 1β-H), 5.37 (2H, m, 22-H and 23-H), and 5.53 (1H, m, 6-H).

(22E,25ξ)-1α,3β,25-Trihydroxy-26-homocholesta-5,7,22-triene (7)

A solution of the 5,22-diene (6) (38 mg, 0.0739 mmol) and N-bromosuccinimide (19 mg, 0.107 mmol) in carbontetrachloride (3 ml) was refluxed under argon for 20 min. After cooling to 0° C., the resulting precipitate was filtered off. The filtrate was concentrated below 40° C. to leave the residue. The THF (5 ml) solution of this residue was treated with a catalytic amount of tetra-n-butyl ammonium bromide at room temperature for 50 min. Then, the mixture was treated with a solution of tetra-n-butylammonium fluoride in THF (0.3 ml, 0.3 mmol) at room temperature for 30 min. The usual work-up (ethyl acetate for extraction) gave a crude triene. This triene in THF (5 ml) was treated with 5% KOH-MeOH (4 ml) at room temperature for 14 hr. The usual work-up (ethyl acetate for extraction) gave a crude product, which was submitted to preparative thin layer chromatography (benzene-ethyl acetate, 1:1, developed six times). The band of Rf value 0.45 was scraped off and eluted with ethyl acetate. Removal of the solvent provided the 5,7,22-triene (7) (8.7 mg, 40%). UV$\lambda_{max}^{EtOH}$: 293, 282, 271 nm.

(22E,25ξ)-1α,25-Dihydroxy-22-dehydro-26-homovitamin D₃ (8)

A solution of the triene (7) (4.4 mg, 0.0103 mmol) in benzene (90 ml) and ethanol (40 ml) was irradiated with a medium pressure mercury lamp through a Vycor filter at 0° C. under argon for 2.5 min. The reaction mixture was refluxed under argon for 1 hr. Removal of the solvent under reduced pressure gave a crude product, which was submitted to preparative thin layer chromatography (benzene-ethyl acetate, 1:1, developed six times). The band of Rf value 0.49 was scraped off and eluted with ethyl acetate. Removal of the solvent provided the vitamin D₃ analogue (8) (0.91 mg, 21%). UV$\lambda_{max}^{EtOH}$: 265 nm, $\lambda_{min}^{EtOH}$: 282 nm. MS m/z: 428 (M+), 410, 392, 374, 338, 320, 287, 269, 251, 141, 134, 123, 73. ¹H-NMR (400 MHz) δ: 0.56 (3H, s, 18-H₃), 0.91 (3H, t, J=7.6 Hz, —CH₂C$\underline{H}$₃), 1.04 (3H, d, J=6.8 Hz, 21-H₃), 1.13 (3H, s, 27-H₃), 4.23 (1H, m, W$_{\frac{1}{2}}$=18.4 Hz, 3α-H), 4.43 (1H, m, W$_{\frac{1}{2}}$=16.9 Hz, 1β-H), 5.00 (1H, bs, W$_{\frac{1}{2}}$=3.2 Hz, 19-H), 5.32 (1H, bs, W$_{\frac{1}{2}}$=3.2 Hz, 19-H), 5.37 (2H, m, 22-H and 23-H), 6.02 (1H, d, J-11.5 Hz, 7-H), and 6.38 (1H, d, J=11.5 Hz, 6-H).

(25ξ)-1α,3β-Diacetoxy-25-hydroxy-26-homocholest-5-ene (9)

A mixture of the 5,22-diene (6) (35 mg, 0.0681 mmol) and 10% Pd-C (4 mg) in ethyl acetate (4 ml) was stirred at room temperature under hydrogen for 3 hr. The Pd catalyst was filtered off and the filtrate was concentrated to leave the residue, which was submitted to preparative thin layer chromatography (hexane-ethyl acetate, 2:1, developed once). The band of Rf value 0.46 was scraped off. Elution with ethyl acetate provided the 5-ene (9) (30 mg, 85%) as an amorphous solid. ¹H-NMR δ: 0.66 (3H, s, 18-H₃), 0.88 (3H, t, J=7 Hz, —CH₂C$\underline{H}$₃), 1.08 (3H, s, 19-H₃), 1.12 (3H, s, 27-H₃), 2.02 (3$\overline{H}$, s, acetyl), 2.04 (3H, s, acetyl), 4.97 (1H, m, 3α-H), 5.04 (1H, m, 1β-H), and 5.51 (1H, m, 6-H).

(25ξ)-1α,3β,25-Trihydroxy-26-homocholesta-5,7-diene (10)

The 5-ene (22 mg, 0.0426 mmol) was converted, as described for (7), to the 5,7-diene 10 (6.7 mg, 37%). UV$\lambda_{max}^{EtOH}$: 293, 282, 271 nm.

(25ε)-1α,25-Dihydroxy-26-homovitamin D₃ (11)

The diene (10) (4.8 mg, 0.0112 mmol) was converted, as described for (8), to the vitamin D₃ analogue (11) (1.3 mg, 27%). UV$\lambda_{max}^{EtOH}$: 265 nm, $\lambda_{min}^{EtOH}$: 228 nm. MS m/z: 430 (M+), 412, 394, 379, 376, 287, 269, 251, 152, 134, 116, 73, 55.

If desired, the compounds of this invention can be readily obtained in crystalline form by crystallization from suitable solvents, e.g. hexane, ethers, alcohols, or mixture thereof as will be apparent to those skilled in the art.

In the above examples, column chromatography was effected using silica gel (E. Merck, Kieselgel 60, 70-230 mesh). Preparative thin layer chromatography was carried out on precoated plates of silica gel (E. Merck, Kieselgel 60 F₂₅₄, 0.25 mm thickness). The usual work-up refers to dilution with water, extraction with an organic solvent, indicated in parenthesis, washing the extract to neutrality, drying over anhydrous magnesium sulphate, filtration, and removal of the solvent under reduced pressure. The following abbreviations were used; THP—tetrahydropyranyl; THF—tetrahydrofuran; ether—diethyl ether, MeOH—methanol, MOM—methoxymethyl, LDA—lithium diisopropyl amide. Temperatures are in ° centigrade.

What is claimed is:

1. A method for inducing and enhancing cell differentiation in malignant cells which comprises exposing said cells to at least one 1 alpha-hydroxylated vitamin D derivative having the structure

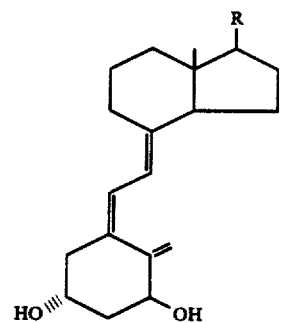

where R is a homo-steroid sidechain selected from the group consisting of

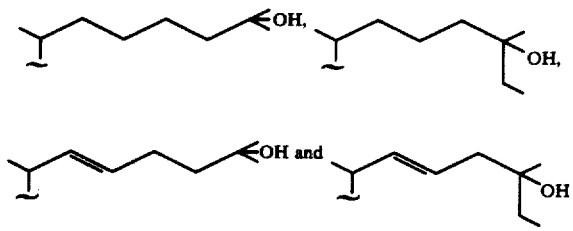

in a molar concentration no greater than about 1×10⁻⁸ moles/liter but in an amount sufficient to induce and enhance cell differentiation.

2. The method of claim 1 where the 1α-hydroxyvitamin D compound is 1α,25-dihydroxyvitamin-24-homovitamin D₃.

3. The method of claim 1 where the 1α-hydroxyvitamin D compound is 1α,25-dihydroxy-22E-dehydro-24-homovitamin D₃.

4. The method of claim 1 where the 1α-hydroxyvitamin D compound is 1α,25-dihydroxy-26-homovitamin D₃.

5. The method of claim 1 where the 1α-hydroxyvitamin D compound is 1α,25-dihydroxy-22E-dehydro-26-homovitamin D₃.

6. A method for treating neoplastic diseases which comprises administering to a patient having a neoplastic disease a compound characterized by a high antineoplastic to calcemic activity ratio having the structure

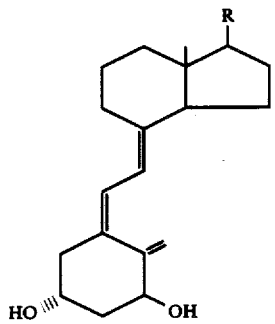

where R is a homo-steroid sidechain selected from the group consisting of

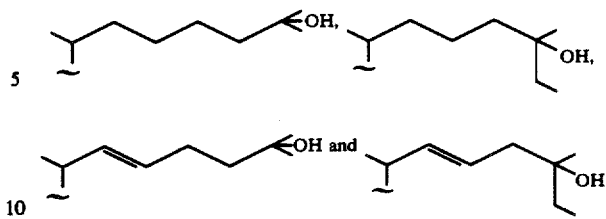

in an amount that results in a blood serum concentration no greater that about $1 \times 10^{-8}$ moles/liter but in an amount sufficient to induce the differentiation of malignant cells to macrophages.

7. A method according to claim 6 where the vitamin D derivative is $1\alpha,25$-dihydroxy-24-homovitamin $D_3$.

8. A method according to claim 6 where the vitamin D derivative is $1\alpha,25$-dihydroxy-22E-dehydro-24-homovitamin $D_3$.

9. A method according to claim 6 where the vitamin D derivative is $1\alpha,25$-dihydroxy-26-homovitamin $D_3$.

10. A method according to claim 6 where the vitamin D derivative is $1\alpha,25$-dihydroxy-22E-dehydro-26-homovitamin $D_3$.

* * * * *

UNITED STATES PATENT OFFICE
CERTIFICATE OF CORRECTION

Patent No. 4,717,721　　　　　　　Dated January 5, 1988

Inventor(s) DeLuca, Schnoes, Ikekawa, and Ostrem

It is certified that error appears in the above-identified patent and that said Letters Patent are hereby corrected as shown below:

In Process Scheme I, compound 2R=THP, and 3R=H, change

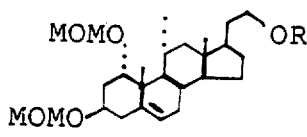　　to　　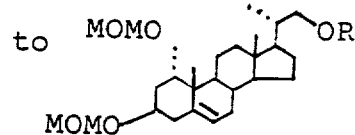

In Process Scheme II, compound 8, change to

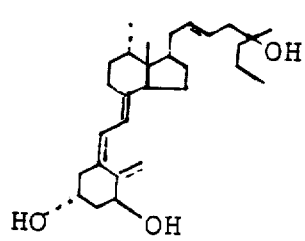　　　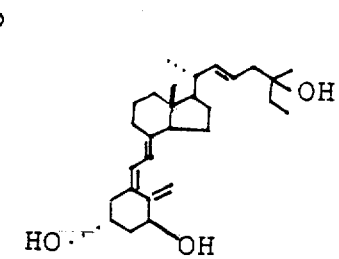

Signed and Sealed this

Twenty-first Day of June, 1988

Attest:

DONALD J. QUIGG

Attesting Officer

Commissioner of Patents and Trademarks